(12) United States Patent
Abjanic

(10) Patent No.: US 6,732,175 B1
(45) Date of Patent: May 4, 2004

(54) NETWORK APPARATUS FOR SWITCHING BASED ON CONTENT OF APPLICATION DATA

(75) Inventor: John B. Abjanic, San Diego, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 09/549,041

(22) Filed: Apr. 13, 2000

(51) Int. Cl.[7] .............................................. G06F 15/16
(52) U.S. Cl. ...................... 709/227; 709/224; 709/203; 707/203; 707/513; 715/513
(58) Field of Search ................................ 709/223, 227, 709/246; 715/511, 512, 513; 707/512, 513, 523, 203

(56) References Cited

U.S. PATENT DOCUMENTS

| | | | |
|---|---|---|---|
| 5,634,010 A | | 5/1997 | Ciscon et al. |
| 5,678,010 A | | 10/1997 | Pittenger et al. |
| 5,862,328 A | * | 1/1999 | Colyer ....................... 709/203 |
| 5,862,344 A | | 1/1999 | Hart |
| 5,870,605 A | | 2/1999 | Bracho et al. |
| 5,896,379 A | | 4/1999 | Haber |
| 5,937,165 A | | 8/1999 | Schwaller et al. |
| 5,951,650 A | | 9/1999 | Bell et al. |
| 5,956,339 A | | 9/1999 | Harada et al. |
| 5,987,500 A | | 11/1999 | Arunchalam |
| 6,006,264 A | * | 12/1999 | Colby et al. ................. 709/226 |
| 6,012,098 A | * | 1/2000 | Bayeh et al. ................ 709/246 |
| 6,032,190 A | | 2/2000 | Bremer et al. |
| 6,091,724 A | | 7/2000 | Chandra et al. |
| 6,167,448 A | * | 12/2000 | Hemphill et al. ........... 709/224 |
| 6,226,675 B1 | * | 5/2001 | Meltzer et al. .............. 709/223 |
| 6,266,335 B1 | * | 7/2001 | Bhaskaran ................... 370/399 |
| 6,343,738 B1 | * | 2/2002 | Ogilvie ....................... 235/381 |
| 6,408,311 B1 | * | 6/2002 | Baisley et al. ............... 707/203 |
| 6,480,860 B1 | * | 11/2002 | Monday ...................... 707/102 |
| 6,480,865 B1 | * | 11/2002 | Lee et al. .................... 715/523 |
| 6,507,856 B1 | * | 1/2003 | Chen et al. .................. 715/513 |
| 6,507,857 B1 | * | 1/2003 | Yalcinalp .................... 715/513 |
| 6,584,459 B1 | * | 6/2003 | Chang et al. .................. 707/3 |
| 2002/0073399 A1 | * | 6/2002 | Golden ........................ 717/114 |
| 2002/0099734 A1 | * | 7/2002 | Yassin et al. ................ 707/513 |

OTHER PUBLICATIONS

International Search Report, European Patent Office, Date of Mailing: Mar. 27, 2002, International application No.: PCT/US 01/10383, International filing date: Mar. 29, 2001, pp. 1–3.

"The Advantages of F5's HTTP Header Load Balancing Over Single–Point URL Parsing Solutions", F5 Networks, Inc. (http://f5.com/solutions/whitepapers/http.html).

"Enabling Software to Speak the Language of Business", Microsoft Corporation, Jan. 7, 2000, BizTalk Framework 1.0a Independent Document Specification.

"SOAP: The Simple Object Access Protocol", Aaron Skonnard, msdn online, Jan. 2000 (http://www.microsoft.com/mind/0100/soap/soap.asp.

"Bluestone Integration Server", Bluestone Products (http://www.bluestone.com/SEalSAPI.dll/ SaServletEngine.class/products/dynamic.jsp?pid=60.

* cited by examiner

Primary Examiner—David Wiley
Assistant Examiner—Phuoc H. Nguyen
(74) Attorney, Agent, or Firm—Blakely, Sokoloff, Taylor & Zafman LLP

(57) ABSTRACT

A network apparatus is provided between a network and a plurality of processing nodes or servers. The network apparatus includes a content based message director (e.g., XML director) to route or direct messages received from the network to one of the processing nodes based upon the application data, including business transaction information

6 Claims, 6 Drawing Sheets

NETWORK APPARATUS FOR SWITCHING BASED ON CONTENT OF APPLICATION DATA

FIELD

The invention generally relates to computers and computer networks and in particular to a network apparatus for switching based on the content application data, such as transaction information.

BACKGROUND

While increasingly more successful in their roles as store and forward data systems, computer networks such as the Internet are experiencing tremendous growth as transaction-based, mission critical business applications, Web site owners, and business servers are overwhelmed by explosive traffic growth. The traditional approach is to buy more servers and network bandwidth. There is typically no distinction between levels of service, but rather a first-in first-out (FIFO) best efforts approach has been the default. However, this has resulted in uneven performance and undifferentiated service. Clearly, there is a need for a technique to allow service providers to intelligently offer different services and different levels of service depending on the circumstances.

Systems are available that allow messages to be routed based upon headers or header information. For example, in Hypertext Transfer Protocol (HTTP), a Post request method includes a request line, a header (or one or more headers) and a body. The request line includes a pointer to a requested resource or program to process the message, such as a Universal Resource Identifier (URI) or Universal Resource Locator (URL). The HTTP header may also include the type of message, the length of the body, and the date. There are systems that parse or examine the URL (i.e., the request line) and/or the HTTP header, and then route the message to a destination node based on the URL and/or header. One such system is described in "The Advantages of F5's HTTP Header Load Balancing Over Single-Point URL Parsing Solutions." However, this approach is very limited as switching decisions are based only on the HTTP header and/or URL.

Another system, known as BizTalk™, improves slightly on the URL parsing technique by providing a system that is compatible with XML-based messages.

XML, or eXtensible Markup Language v. 1.0 was adopted by the World Wide Web Consortium (W3C) on Feb. 10, 1998. XML provides a structured syntax for data exchange. XML is a markup language, like HTML. Most markup languages, like HTML, are fixed markup languages. That is, the fixed markup languages (including HTML) include a set of fixed tags for crafting a document. On the other hand, XML does not define a fixed set of tags, but rather, only defines a syntax or structured format through which users can define their own set of XML tags. There presently are a number of XML based languages which define their own set of tags using the XML syntax. XML has the further advantage because the actual data is separated from the presentation of the data, in contrast with HTML which combines these two items. As a result, XML has the potential to become a standard by which most computers, servers and applications will exchange or communicate data.

As described in "BizTalk Framework 1.0a Independent Document Specification," Microsoft Corp., Jan. 7, 2000, BizTalk defines a specific set of tags (or BizTags) within a message that are used to specify business document handling (p.7). A Biztalk server uses information contained in the Biztags to determine the correct transport-specific destination address(es). (pp. 9, 11). However, the tags used to mark up business transaction information within the message body are determined by the individual implementation. These implementation-specific tags (provided in the content or business transaction information of the message body) are not considered BizTags (p. 11).

There are a number of disadvantages to such an approach. The BizTalk system is very limited because it can route or switch messages based only upon header or introductory information, based upon the fixed set of the BizTalk tags. The BizTalk system does not make decisions or route/switch messages based upon the actual content or business information (e.g., business transaction information) within the message body. Moreover, to provide routing or address information, the Biztalk system requires that messages conform to the required format for the fixed set of Biztags, which is very inflexible and will likely inhibit the routing or switching of messages provided according to the other XML based languages (e.g., CXML, WML). Finally, many processing nodes, application servers and the like are presently burdened with a number of activities, such as establishing connections, communicating and processing requests for business related information, purchase orders, invoices or other business transactions. Further burdening a server with routing or switching decisions will require significant application processing cycles or bandwidth. This may overburden the server or negatively impact the server's ability to adequately handle business transactions.

BRIEF DESCRIPTION OF THE DRAWINGS

The foregoing and a better understanding of the present invention will become apparent from the following detailed description of exemplary embodiments and the claims when read in connection with the accompanying drawings, all forming a part of the disclosure of this invention. While the foregoing and following written and illustrated disclosure focuses on disclosing example embodiments of the invention, it should be clearly understood that the same is by way of illustration and example only and is not limited thereto. The spirit and scope of the present invention is limited only by the terms of the appended claims.

The following represents brief descriptions of the drawings, wherein.

DETAILED DESCRIPTION

According to an example embodiment, a network apparatus is provided between a network and a plurality of processing nodes (e.g. web servers, application servers, fulfillment servers, XML servers, routers, switches or other devices). The network apparatus includes a content based message director (e.g., a XML director) to route or direct messages received from the network to one of the processing nodes based upon the content of the application data in the message, including business transaction information. The application data (including business transaction information) may advantageously be provided as a XML based language.

The application data may be transmitted or received via a cell, packet or other envelope. The application data (such as business transaction information) is data to be processed by an application or program running on an application server, an XML server (which processes XML documents) or other processing node. Business transaction information can include a wide variety of application level information or transaction information such as purchase orders, invoices, inventory requests or replies, stock quotes, stock trade requests or confirmations, bids, transaction confirmations, shipping/delivery instructions or requests, materials or resource usage indications or measurements, information related to a transaction and its many details, etc.

According to one or more embodiments, the network apparatus includes many advantages. First, by examining well beyond a request line (e.g., URL) and message headers and into the content of the application data (such as the business transaction information) of a message, businesses can provide improved differentiation of services and different service levels for received requests and messages based upon the business transaction information in the messages. Second, by providing the content based message director (or XML director) as a network apparatus located between the network and one or more processing nodes or application servers, the burden of examining the application data or business transaction information and then switching to a particular processing node (e.g., performing XML switching) is offloaded from application servers to a network apparatus (e.g., network appliance, network processor, network server, or the like). Also, the content based message director (or XML director) can receive and switch messages based upon application data or business transaction information regardless of the transport or protocol used to transport the message (e.g., the director is transport independent). Finally, the XML director is not limited to receiving and processing XML data according to a set of fixed tags, but rather, is compatible with any of the XML based languages.

Figure 1:
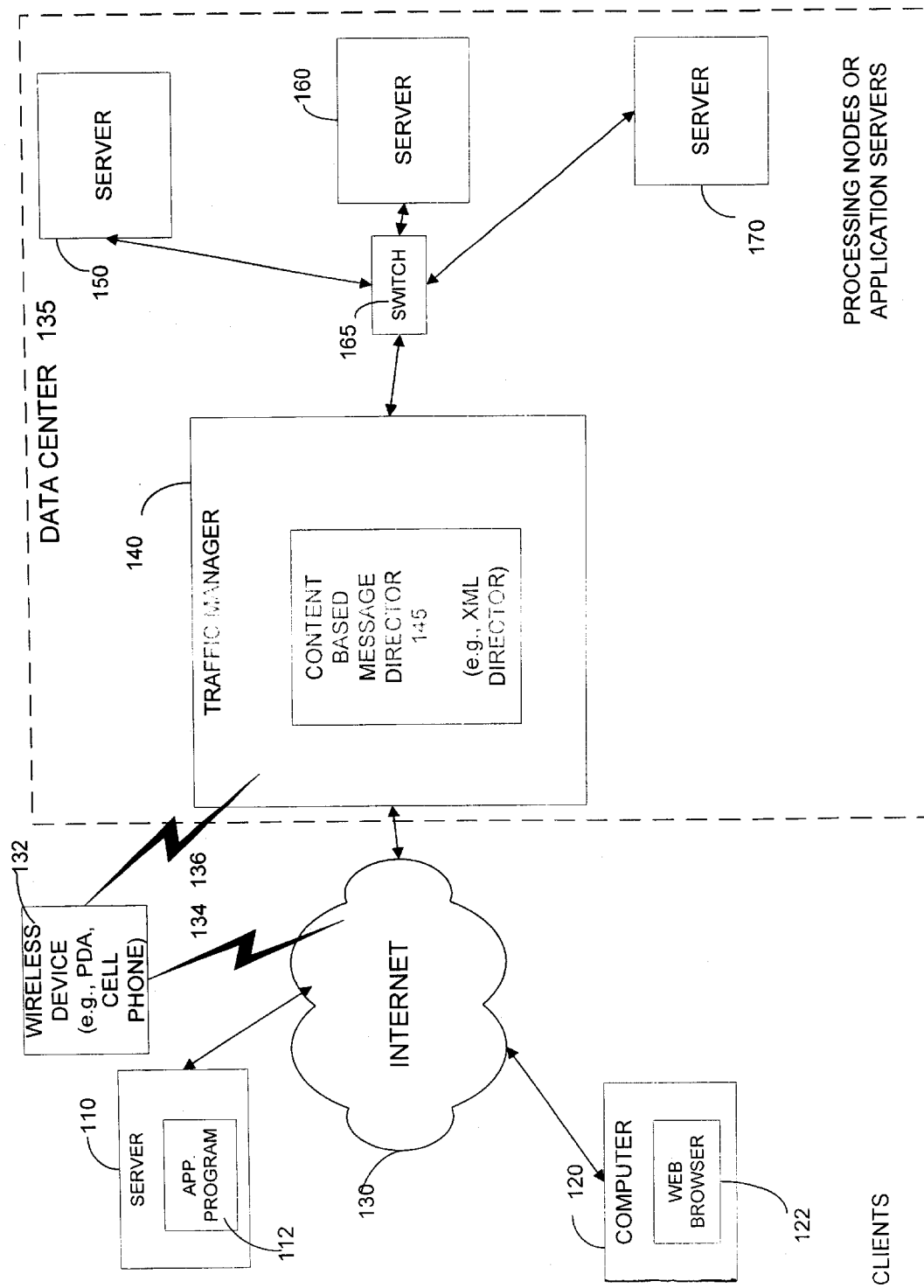
FIG. 1 is a block diagram of a network system according to an example embodiment.

Referring to the Figures in which like numerals indicate like elements, FIG. 1 is a block diagram of a network system according to an example embodiment. As shown in FIG. 1, a variety of clients may be coupled or connected to a data center 135 via a network, such as the Internet 130. The clients, for example, may include a server 110 that includes an application program 112, a computer 120 (such as a personal computer or laptop) that may include a web browser 122 and a wireless device 132, such as a personal digital assistant (PDA) or a wireless (or cellular) telephone. Wireless device 132 may be coupled to the Internet 130 or to a data center 135 via communications links 134 and 136, respectively. Links 134 and 136 each may include one or more of a wireless link (e.g., cellular or other link) or a wireline link. Each of the clients, including server 110, computer 120 and device 132 can send and receive messages over the Internet 130 and may use a variety of different protocols or transports.

The data center 135 is provided for sending, receiving and processing a wide variety of messages, requests, business transactions, purchase orders, stock quotes or stock trades, and other information. The data center 135 includes several processing nodes (e.g., servers), including server 150, server 160 and server 170 for handling the various orders, business transactions and other requests. The different servers in data center 135 may be allocated to provide different services, or even different levels of services. According to an example embodiment, the clients and the data center 135 exchange business transaction information or other information by sending and receiving XML messages (data provided in XML or in a XML based language), or messages based upon another type of structured syntax for data interchange.

The various servers (e.g., servers 150, 160 and 170) are coupled to a traffic manager 140 via a switch 165. Traffic manager 140 may perform a variety of functions relating to the management of traffic, including load balancing (e.g., balancing the load of incoming messages or requests across the available servers according to some policy, such as round-robin, least number of connections, or other load balancing technique).

Referring to the clients again in FIG. 1, application program 112 may be a business program or a program for managing inventory, orders or other business transactions. For example, application program 112 may automatically and electronically detect that inventory has decreased below a threshold value and then automatically generate and send a purchase order to a supplier's server at data center 135 to request a shipment of additional supplies or inventory. Thus, server 110 may initiate, for example, a business-to-business (B2B) transaction by sending an electronic order to the supplier's remote server located at data center 135.

As a another example, web browser 122 may request web pages, business information or other information from a remote server (e.g., located at data center 135). Web browser 122, may also send or post purchase orders, business transactions or other business information to a remote server, which may be located at data center 135. Wireless device 132 may receive information or data related to purchase orders, business transactions, web pages, stock quotes, game scores and the like from one or more remote servers (such as servers located at data center 135).

According to an embodiment, the server 110, computer 120 and wireless device 132 each may communicate or interchange data with one or more remote servers (e.g., servers 150, 160 and 170) by sending and receiving XML data (i.e., application data that is encoded or formatted according to the XML standard or according to one or more XML based languages).

According to an example embodiment, the traffic manager 140 includes a content based message director 145 to direct or switch messages to a selected server based upon the content of application data, such as business transaction information (which may be provided as XML data). Traffic manager 140 and/or message director 145 may be software, hardware or a combination of both, and may even be provided on or as part of a network processor. It should be noted that director 145 may operate by itself, or as part of a larger network apparatus, such as part of a traffic manager 140.

According to an example embodiment, because of the advantages of XML, application data can advantageously exchanged between the servers of data center 135 and one or more clients or computing nodes by sending and receiving messages that include application data that is encoded or formatted according to the XML standard. Therefore, according to an embodiment, director 145 may be a XML director because it directs (or routes/switches) the incoming message to a particular server based upon the XML data in the message. The XML data preferably complies with the format or syntax required by the XML standard. A document that uses tag formats (e.g., start tags, end tags) and other syntax (e.g., to markup data) that complies with the XML standard is considered to be a "well-formed" XML document.

Therefore, in an exemplary embodiment, content based message director 145 is a XML director. However, it should be understood that director 145 can direct or switch messages having basically any type of structured syntax, including any type of markup language.

An advantageous aspect of the embodiment of the traffic manager 140 and director 145 shown in FIG. 1 is that the traffic manager 140 and the director 145 are located in front of the one or more application servers or processing nodes. By locating the traffic manager 140 and director 145 in a computer, server or computing system in front of the processing nodes or servers (as shown in FIG. 1) (e.g., coupled between the network 130 and the servers), the traffic management functionality and the functionality of the director 145 can be off-loaded from an application server to a separate and/or dedicated network apparatus or network system. This can advantageously relieve the processing nodes or application servers from this additional processing overhead.

Figure 2:
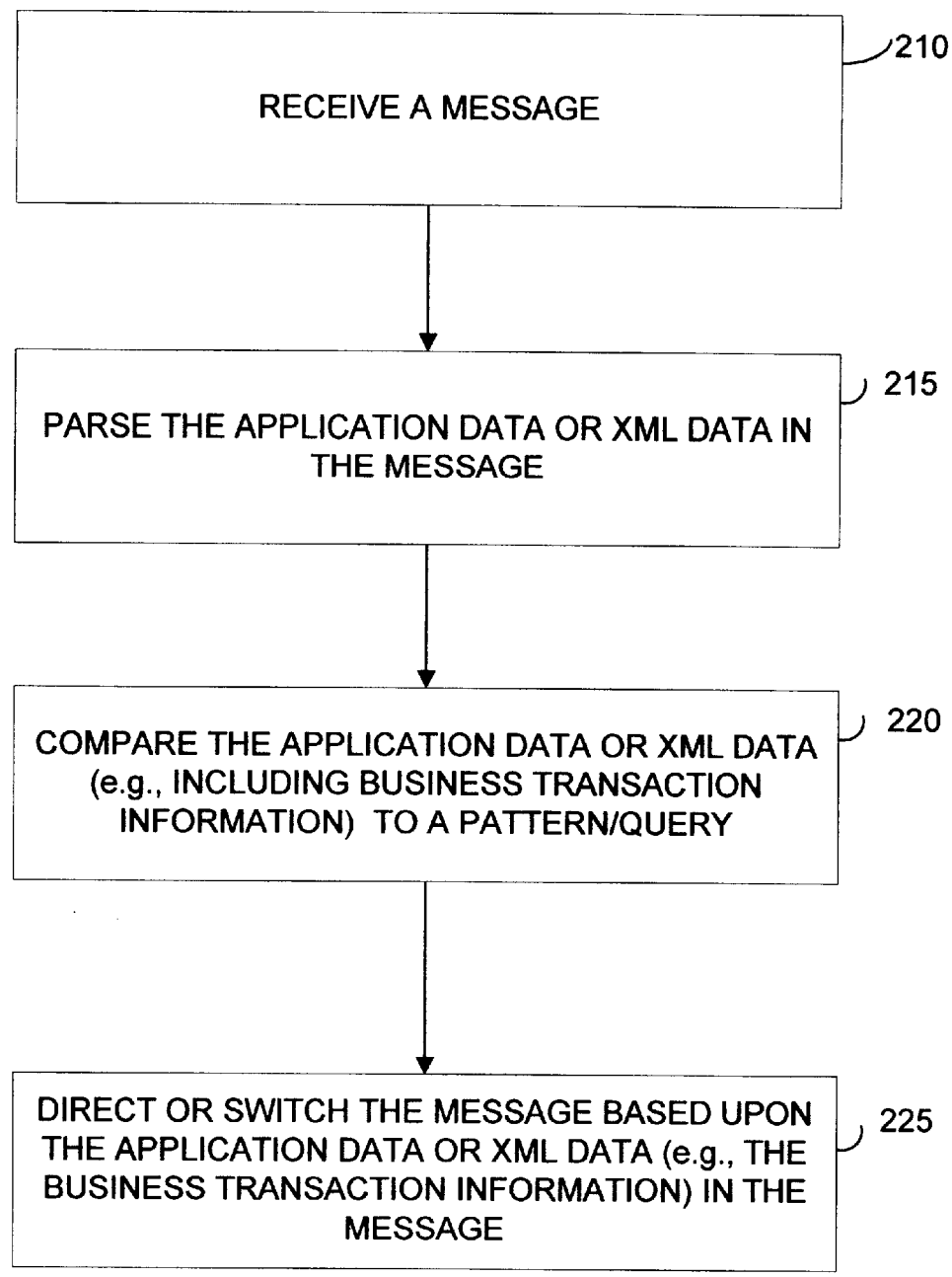
FIG. 2 is a flow chart illustrating an operation of content based message director according to an example embodiment.

FIG. 2 is a flow chart illustrating an operation of content based message director according to an example embodiment. At block 210, the director 145 receives a message. The message may be sent over any transport or protocol(s), such as Transmission Control Protocol (TCP), File Transfer Protocol (FTP), Simple Mail Transfer Protocol (SMTP), Wireless Application Protocol (WAP, which may be used to send and receive information with wireless devices), Hypertext Transfer Protocol (HTTP), etc. The general teachings and the operation of the invention are not dependent upon any particular transport or protocol, but rather are transport-independent.

A HTTP Post is an example of a message. The format for an HTTP Post message (or HTTP request) may be presented as:

request-line (the URL); identifies a program for processing the message
headers (0 or more)
<blank line>
body (the application data or the XML data; only for a POST)

Here's an example:

POST www;acme.com/purchasing/order.cgi HTTP/1.1
Content-Type: text/xml
Content-Length: 1230
User-Agent: Cern-Line Mode/2.15
Date: 3/27/00

<XML>
<From>intel.com</From>
<To>bookstore.com</To>
<PurchaseBook>
  <ISBN>02013798233</ISBN>
  <PurchaseAmount> 98</PurchaseAmount>
</PurchaseBook>
</XML>

In this example, the URL (or request line) is provided in a request line to identify a program or application to process the message. Several header lines (Content-type, Content-length, date, etc.) make up an HTTP header. The application data is provided after the HTTP header, and in this example is provided as XML data. A start tag <XML>, and </XML>, an end tag, identify the start and end, respectively, of the application data (or XML data). This XML application data is also referred to as a XML document. The XML document includes markup characters (or tags) which describe data, and data characters. As an example, a "To" element of the above XML document is written as: <To>bookstore.com</To>. Where<To> is a start Tag and </To> is an end tag, which are markup characters because they describe the XML data characters (bookstore.com). The business transaction information describes the business transaction (To, From, items purchased, purchase amount, quantity, etc.), and is not included in the URL, the HTTP header, or any other header (e.g., IP header, TCP header) of the envelope used for sending the message.

While the prior art performed switching based on the request line or URL and/or the HTTP header, the present invention is directed to a technique to perform switching at a network apparatus based upon the application data, such as XML data (which includes business transaction information).

In this example message, the business transaction information provided within the application data as XML data relates to the transaction or describes the transaction, including, for example, what kind of business transaction (a purchase order or to purchase a book), who it is from and who it is to, an ISBN number to identify the goods to be purchased and the amount of the purchase (PurchaseAmount). These are merely examples of the types of business transaction information in a message upon which the director 145 can analyze and make routing or switching decisions for the message.

At block 215 of FIG. 2, the director 145 (FIG. 1) parses all or part of the application data (the XML data in this example) and can check to ensure that the XML document or application data is well formed (i.e., checks to make sure at least a portion of the XML document meets the so-called well-formedness constraints or requirements in the XML specification or standard). Parsing generally refers to the process of categorizing the characters or XML data that make up the XML document as either markup (e.g., <To>) or character data (e.g., bookstore.com).

At block 220 of FIG. 2, the application data or XML data (including markup characters and/or character data) is then compared to one or more configuration patterns or queries (which may be stored in the director 145) to determine if there is a match. According to an embodiment, the configuration patterns may be dynamically changed or updated by a user or by a program or application. For example, a program may detect the failure of one or more servers and/or detect the response time of servers, and then update the configuration pattern to account for these changes in the network (e.g., redirect certain messages from busy servers to servers which are less busy, or from servers which have failed to the available servers).

At block 225, if there is a match between the content of the application data (e.g., the business transaction information which may be provided as XML data) of a message and a configuration pattern or query, then the director 145 directs or switches the message to the corresponding server (or processing node) in the data center (e.g., directed to the specific server as indicated by the configuration pattern). If there are multiple matches, the director 145 can just direct the message based to the first match, or a load balancing policy can be used to balance messages among a group of servers. If there is no match, the message can be directed to a default server or can be blocked. Alternatively, the configuration pattern can also identify a certain pattern for which a message should be blocked from being forwarded. In this respect, the director 145 may also act as a filter to selectively pass or forward some messages while blocking others, based upon the application data.

For example, the director 145 may be configured to direct or switch messages based on the following configuration patterns or queries:

| Server | IP address | Port | XML pattern |
|---|---|---|---|
| S1 (e.g., 150) | 10.1.1.1 | 80 | To = bookstore.com |
| S2 (e.g., 160) | 10.1.1.2 | 80 | To = stockquote.com |
| S3 (e.g., 170) | 10.1.1.3 | 80 | To = computerstore.com |

Based on the above configuration patterns, the director 145 would direct a message to server S1 (having the IP address 10.1.1.1 and port 80) if the data for the To element of the business transaction information is bookstore.com. The message will be directed to server S2 (having an IP address 10.1.1.2 and port 80) if the data for the To element of the business transaction information is stockquote.com. And, the director 145 will direct any messages to server S3 if the data for the To element of the business transaction information is computerstore. com.

This advantageously allows different types of services (or different levels of service) to be provided for messages based on the content of the application data (such as the business transaction information) in the message. In this example, server S1 may be allocated to handle purchase orders for books sent to bookstore.com. Server S2 may be allocated to process requests for real-time stock quotes, while server S3 may be allocated to process purchase orders for computers sent to computerstore.com.

There are many examples where content based switching based upon the content of the application data or business transaction information can be used to offer different or differentiated services or even different or differentiated levels of services. As another example, the director 145 may be configured to direct or switch messages based on the following configuration patterns or queries:

| Server | IP address | Port | XML pattern |
|---|---|---|---|
| S1 (e.g., 150) | 10.1.1.1 | 80 | PurchaseAmount < $100 |
| S2 (e.g., 160) | 10.1.1.2 | 80 | $100 < PurchaseAmount < $1000 |
| S3 (e.g., 170) | 10.1.1.3 | 80 | $1000 < PurchaseAmount |
| S4 (not shown) | 10.1.1.4 | 80 | $1000 < PurchaseAmount |

In this example, messages for purchase orders are sent to server S1 if the purchase amount is less than $100; messages for purchase orders are sent to S2 if the purchase amount is less than $1000 and more than $100; and for the high dollar purchases, the messages for purchase orders for purchases greater than $1000 can be sent to either of two servers. In this fashion, the director 145 (FIG. 1) can direct or route received messages based on the content of the application data or business transaction information in the message. This allows web sites or electronic-businesses (e-businesses) to offer different or differentiated levels of services based on the content of the application data or transaction information.

In this particular example, two servers (S3 and S4) have been allocated to handle the highest dollar purchase orders. Thus, by specifically allocating greater resources (e.g., two or more servers as compared to just one server) for the higher dollar amount purchases as compared to the lower dollar purchases, an e-business operating at data center 135 can provide a higher level of service for purchase order messages having a higher dollar purchase amount. In this manner, director 145 can switch or direct messages to another network device or to a specific server based upon a wide variety of business transaction information or application data.

Figure 3:
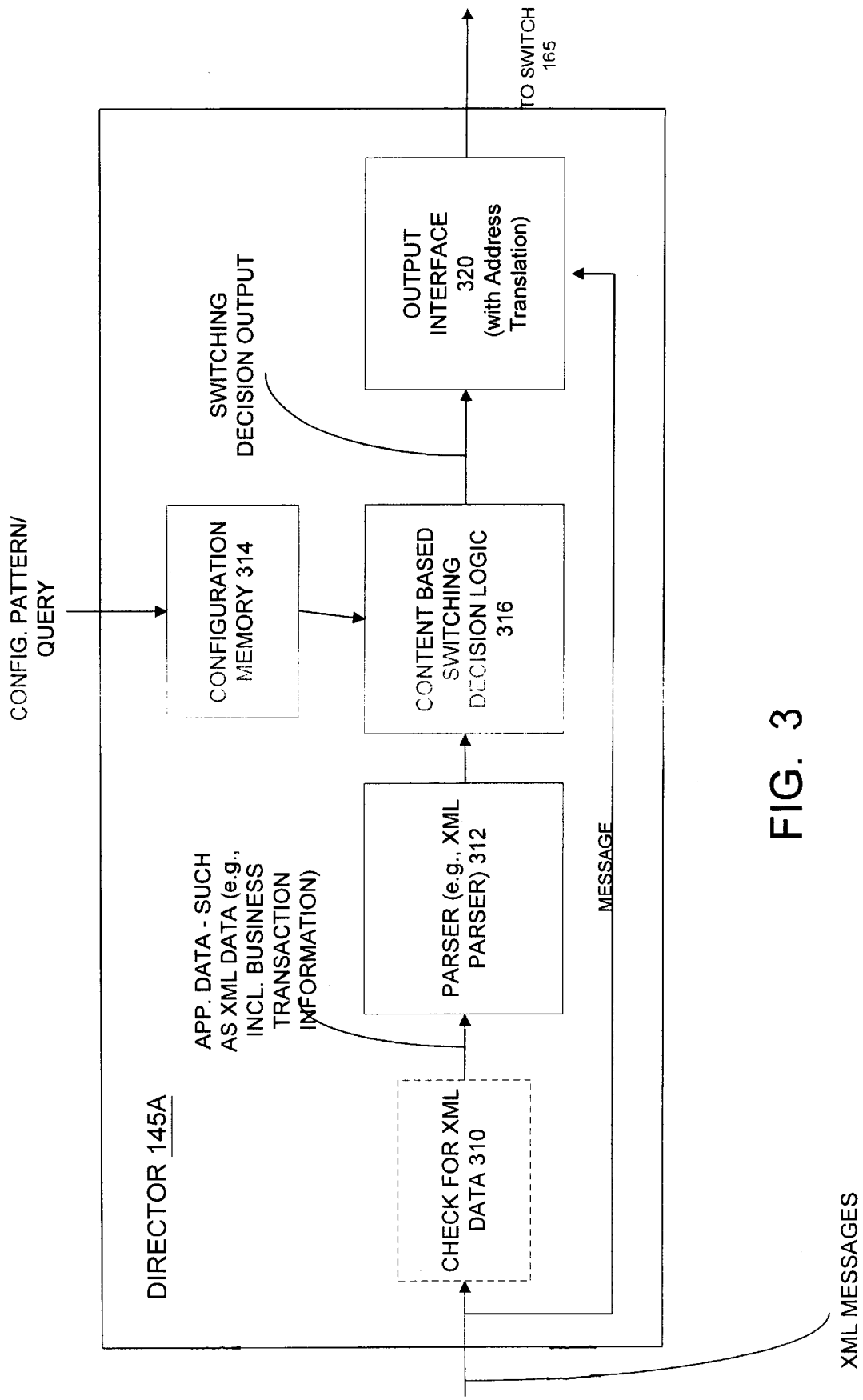
FIG. 3 is a block diagram illustrating a director according to an example embodiment.

FIG. 3 is a block diagram illustrating a director according to an example embodiment. Director 145A includes a block 310 to determine whether a received message includes XML data.

According to an embodiment, if the message does not include XML data, the message will be passed (e.g., directly) through to the output with little if any further processing by director 145A. If the message does include XML data, then the message will be analyzed for making a routing or switching decision as described below.

There are many ways in which block 310 can determine whether a received message includes XML data. According to one embodiment, certain types of filenames (e.g., invoice.cgi) or filename extensions (e.g., *.cgi), which may typically be provided in the request line, may indicate whether the message includes XML data. Thus, the filename extension may be analyzed by block 310 to determine whether the message includes XML data. Other information in the message, including other header information or even a particular tag in the application data itself (e.g., the <XML> start tag) can be used to identify whether or not the message includes XML data.

According to an embodiment, block 310 is optional. However, it is advantageous to provide block 310 where only a small percentage of the incoming messages include XML data. Without block 310, application data for all messages will be parsed and compared to the configuration pattern, and a switching decision will be generated. Thus, for those messages which do not include XML data (and thus cannot be switched or directed by director 145A), director 145A will add unnecessary latency in the message forwarding path in the absence of block 310. On the other hand, where a significant percentage of the messages received by director 145A include XML data, block 310 may be considered unnecessary and may be omitted (because block 310 would typically add unnecessary latency in such case).

A parser 312 is coupled to the output of the block 310 to parse the application data (or a portion thereof). A configuration memory 314 receives and stores one or more configuration patterns or queries. A content based switching decision logic 316 receives the output from the parser 312 and compares the configuration patterns to the application data or business transaction information (e.g., including the data and the markup characters describing the data within the configuration pattern). The content based switching decision logic 316 then outputs a switching or routing decision for the message on the basis of the comparison (i.e., on the basis of the business transaction information). The configuration pattern may indicate both a pattern and a processing node or server to process the message if a pattern is found in the message.

The output interface 320 then switches or directs the message on the basis of this decision (e.g., routes the message to the processing node or server indicated by the matching configuration pattern). For example, if there is no match, the output interface 320 may filter or block the message, or may direct or route the message to a default server or a predetermined server in the data center 135. If a match is found, the output interface 320 switches or directs the message to the appropriate destination (e.g., to the appropriate processing node or server within data center 135).

The configuration pattern may require multiple patterns, or even a hierarchical arrangement of data elements in the application data for a specific match. For example, the decision logic 316 may receive a configuration pattern that specifies:

| Server | IP address | XML pattern |
|---|---|---|
| S1 (e.g., 150) | 10.1.1.1 | From=Intel, and PurchaseAmount < $100 |

In such a case, the switching decision logic 316 would examine the application data (or XML data) to first identify a From tag that is set to Intel. Next, it would examine the transaction information to identify a PurchaseAmount that is less than $100. If both of these are found, this indicates a match.

If a match is found between the business transaction information and the pattern, the content based switching logic 316 outputs a switching decision to a output interface 320. The switching decision may, for example, indicate that a match was found and identify the processing node or server (e.g., by address and port number or other identifier) where the message should be directed.

According to an example embodiment, the decision logic 316 provides an IP address and port number to be used as a new destination IP address and destination port number for the message. The output interface 320 may then translate the destination IP address and port number in the packet or envelope of the received message from the original destination IP address and port number (i.e., the IP address and port. number of the traffic manager 140 or director 145A) to the new destination IP address and port number provided by the decision logic 316. According to an embodiment, the new destination IP address identifies a processing node or server (e.g., within data center 135 or elsewhere) and the new destination port number identifies a program or application on that processing node or server that will receive and process the message.

The message (e.g., with its associated TCP and IP headers translated or modified to include the new destination address and port number) is then output from the director 145 and traffic manager 140. Switch 165 receives the message, and then routes the message to the appropriate processing node or server based on the IP address.

According to an example embodiment, a client (e.g., a server 110, computer 120, etc., FIG. 1) that sends a message first establishes a connection (e.g., a TCP connection), and then sends the message via HTTP (or other transport) to the traffic manager 140 and/or director 145A. The director 145A then parses the XML data, and makes a switching decision based on the business transaction information in the message as compared to one or more configuration patterns. A new connection is then established between the director 145A or traffic manager 140 and the destination processing node or server. The message is then directed or routed from director 145A to the specified node or server.

Figure 4:
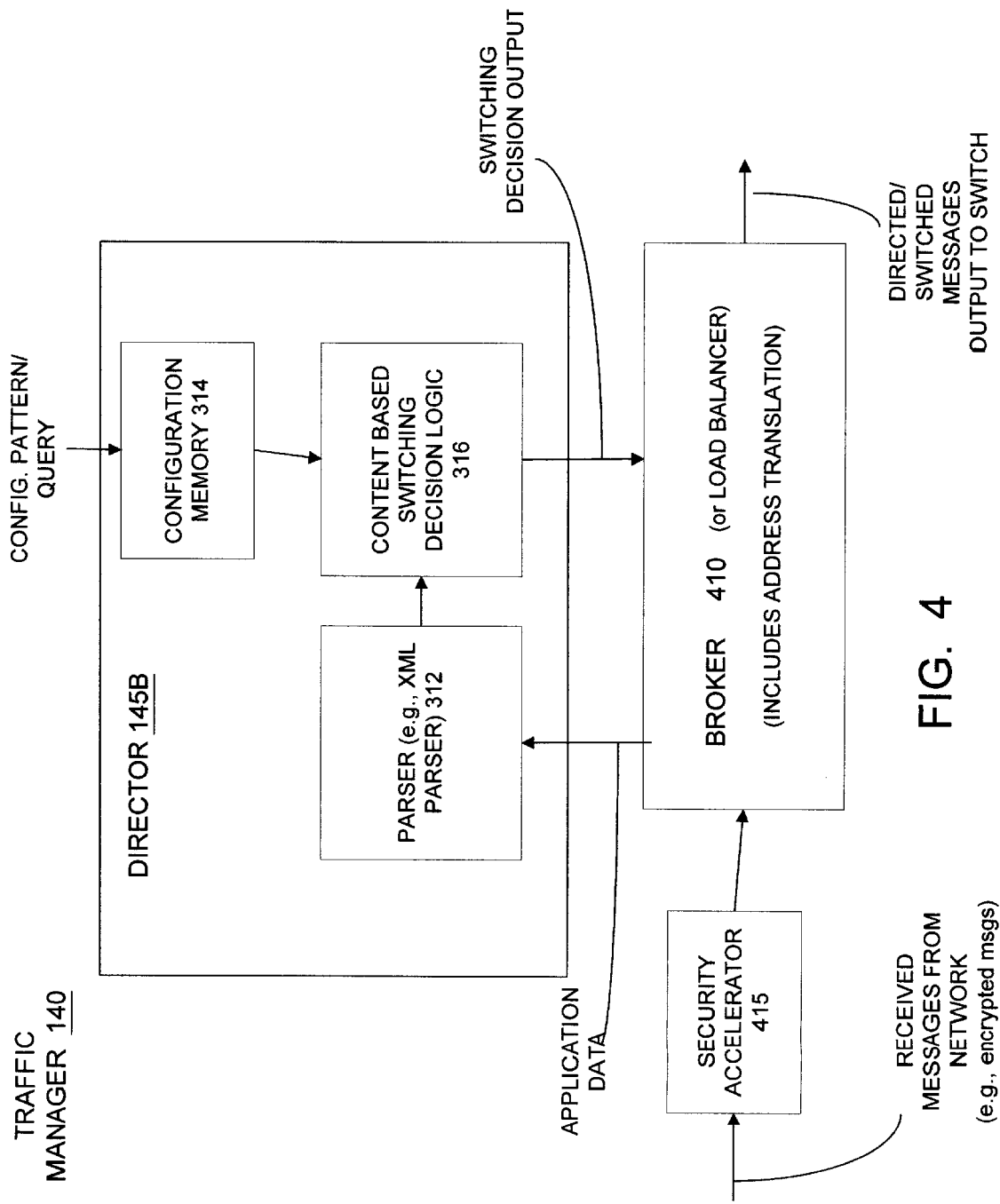
FIG. 4 is a block diagram illustrating a traffic manager according to another example embodiment.

FIG. 4 is a block diagram illustrating a traffic manager according to another example embodiment. Traffic manager 140 includes a security accelerator 415 for encrypting outgoing messages and/or decrypting incoming messages received from the network. According to an embodiment, the security accelerator 415 is a Secure Sockets Layer (SSL) accelerator, available from Intel Corporation. The security accelerator 415 allows the security related tasks such as encryption and/or decryption to be off-loaded from the application server to the accelerator 415 of the traffic manager 140.

Traffic manager 140 also includes a director 145B and a broker 410. A decrypted message is received by broker 410 from security accelerator 415. According to an example embodiment, broker 410 operates as both an output interface (similar to output interface 320) and a load balancer to balance or adjust the traffic among one or more of servers or processing nodes within the data center 135.

Director 145B is similar to director 145A but may not include block 310 and/or the output interface 320 of director 145A (as these functions may be provided by the broker 410 in FIG. 4). Parser 312 (which may be optional) parses the XML data. The content based switching decision logic 316 compares the configuration patterns to the application data or business transaction information in the message and then outputs a switching decision to broker 410 for the message on the basis of the comparison. The switching decision output to broker 410 may, for example, identify the IP address and port number of the selected processing node or server or application server that should receive the message.

Broker 410 performs address translation on the header(s) for the message. The address translation performed by broker 410 includes a destination address and destination port translation and an optional source address and source port translation. The destination address and port translation may be performed by translating the original destination IP address and port number of the received message (which may identify the broker 410) to the IP address and port number of the specified processing node or server (or of the specified server resource or program). In addition, the broker may also translate the source IP address and port number in the packet or envelope from the originating client's address and port number to the IP address and port number of the broker 410 (or of the traffic manager 140). The message (including one or more translated addresses) is then output from broker 410. Switch 165 (FIG. 1) receives the message and forwards the message to the appropriate server based on the destination address in the message. According to one embodiment, it is not necessary to actually translate the source IP address and port number if all return messages or replies from the processing node or server are routed through the broker 410.

Broker 410 also translates destination addresses for return messages or replies from the processing node or server sent to the client, to substitute the IP address and port number of the client as the destination address and port for the return message or reply. Thus, the broker 410 may operate as a gateway or output interface between the client (FIG. 1) and the processing node or server, by performing destination address translation prior to routing or forwarding the message, and performing a similar translation for return or reply messages sent from the processing node or server back to the client.

According to an example embodiment, broker 410 and security accelerator 415 may be provided, for example, as an Intel® NetStructure™ 7180 E-Commerce Director. Alternatively, the broker 410 may be provided as an Intel® NetStructure™ 7170 Traffic Director. Both are available from Intel Corporation, Santa Clara Calif. As a result, broker 410 may perform additional functions including load balancing according to a load balancing policy or algorithm to adjust the load on each server in the data center.

Figure 6:
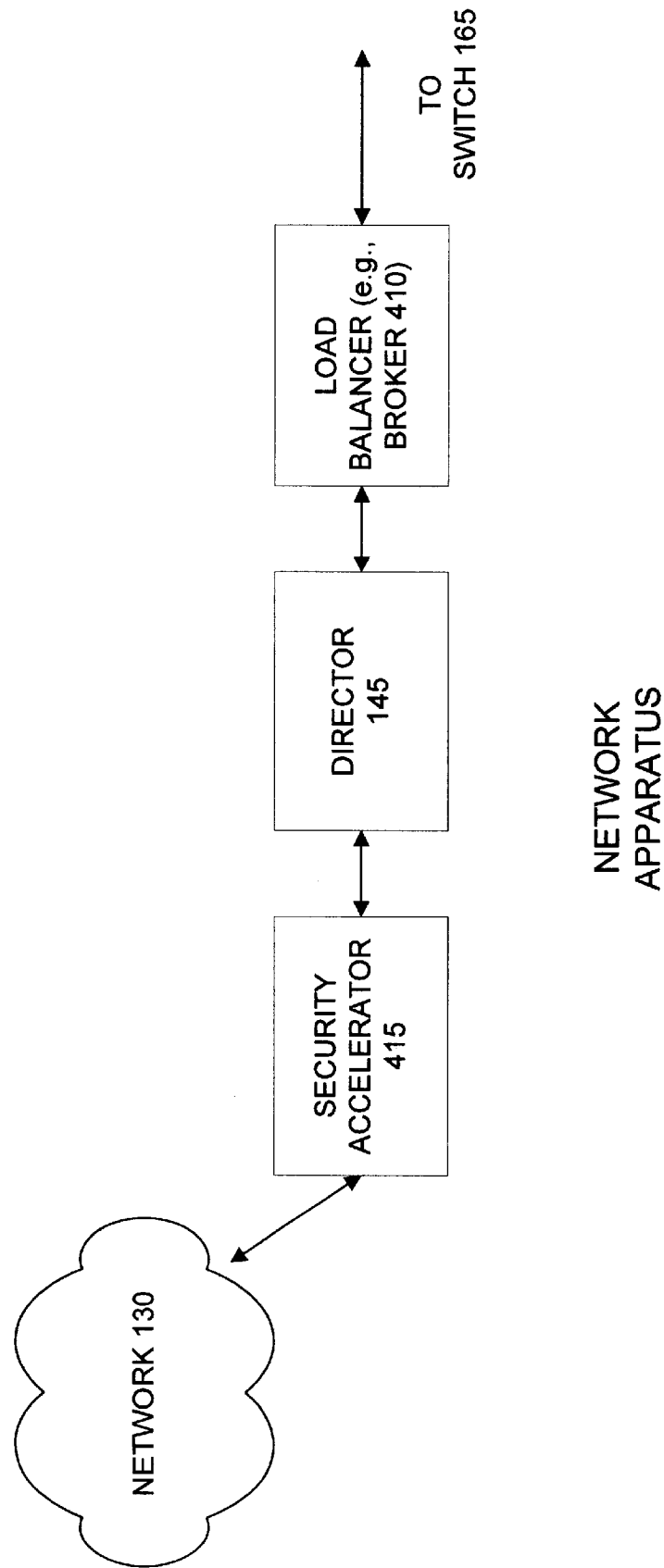
FIG. 6 is a block diagram illustrating a network apparatus according to another example embodiment.

The director 145 (or 145A or B), the security accelerator 415 and the broker 410 (or load balancer) may be provided in a network apparatus in different combinations, depending on the circumstances. FIG. 6 is a block diagram illustrating a network apparatus according to another example embodiment. For example, each of the director 145, security accelerator 415 or load balancer (or broker 410) may be provided by itself. Alternatively, all three of the security accelerator 415, an XML director 145 and a load balancer may be provided within a network apparatus or traffic manager, as shown in FIG. 6. Or, the XML director 145 may be combined with just one of either a security accelerator 415 or a load balancer (broker 410). Other combinations are possible.

Figure 5:
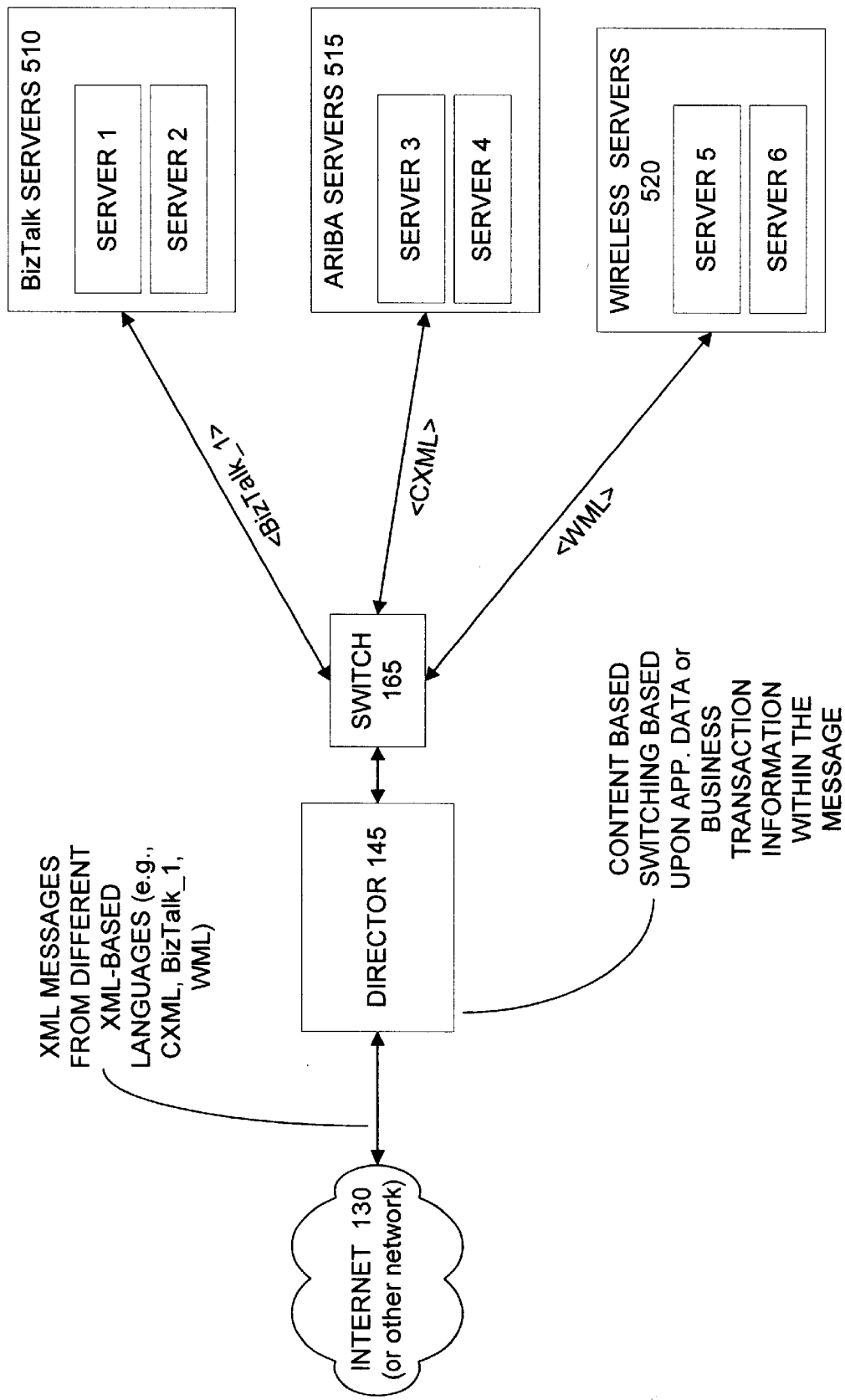
FIG. 5 is a block diagram illustrating another example operating environment for a content based message director according to an example embodiment.

FIG. 5 is a block diagram illustrating another example operating environment for a content based message director 145 according to an example embodiment. As noted above, XML does not define a fixed set of tags, but rather, only defines a syntax or structured format through which users can define their own set of tags or their own XML based language. In fact there are many different XML-based languages in use, each having a unique set of tags that define what elements should be provided to comply with that XML language.

An XML language is defined by a validation template (indicating the proper form for the tags), known in XML as a Document Type Definition (DTD). For example, BizTalk by Microsoft Corp. includes one set of XML tags; CXML by Ariba Corp. includes its own set of tags; CBL by Commerce One includes another set of XML tags; While WML (Wireless Markup Language) defines yet another set of XML tags for the communication or interchange of data to and from a wireless device. Each of these XML-based languages includes a different or unique set of tags, and thus each is generally incompatible with the other languages. For example, a client sending data using CXML will not be able to properly communicate with a processing node or server that expects to receive data only provided according to WML.

According to an advantageous aspect of the present invention, director 145 can receive an XML message, compare the application data or business transaction information to the configuration pattern, and then direct or route the message (or make switching or routing decisions) to an appropriate processing node or server regardless of the type of XML-based language used by the message. Once the director 145 is configured to detect or recognize one or more specific tags and corresponding data (e.g., PurchaseAmount >$100), the director 145 can direct or route the message based on the content of the application data (e.g., based on the business transaction information provided as XML data), regardless of the type of XML-based language that is used by the message.

As shown in FIG. 5, Director 145 is coupled to switch 165. There are three sets of servers (or data centers) coupled to the switch 165, including: a set of BizTalk servers 510 (including servers 1 and 2) which communicate data using an XML based language known as BizTalk; a set of Ariba servers 515 (including servers 3 and 4) which communicate data using the XML based language known as CXML; and a set of wireless servers 520 (including servers 5 and 6) which communicate data using only the XML based language known as Wireless Markup Language or WML. These are merely provided as examples. Thus, the director 145 can operate as a gateway or interface, receiving messages from a variety of different clients using a variety of different XML based languages, and then directing or routing the messages to the appropriate processing node or servers.

Several embodiments of the present invention are specifically illustrated and/or described herein. However, it will be appreciated that modifications and variations of the present invention are covered by the above teachings and within the purview of the appended claims without departing from the spirit and intended scope of the invention.

What is claimed is:

1. An XML director comprising:
   an XML checker to determine whether a received message includes XML information;
   an XML parser coupled to the XML checker to parse XML tranasaction information in the message if the XML checker determines that the message includes XML information;
   a content based switching decision logic coupled to the XML parser to receive one or more configuration patterns, the content based switching decision logic to make a switching decision for the received message based upon a comparison of the one or more configuration patterns to the XML transaction information if the XML checker determines that the message includes XNL information; and
   an output interface coupled to the content based switching decision logic to switch the message to a processing node based upon the switching decision if the message includes XML information, the output interface to switch the message without XML parsing if the message does not include XML information.

2. The XML director of claim 1 wherein the XML director comprises a traffic manager.

3. The XML director of claim 1 wherein the XML director comprises a network processor.

4. The XML director of claim 1 wherein the processing node comprises a server to process requests or business transactions provided in the messages.

5. A data center comprising:
   a plurality of processing nodes to process messages;
   a content based message director coupled between a network and the plurality of processing nodes, the content based message director comprising an XML checker to determine if the message includes XML information, the content based message director comprising a content based switching decision logic to make a switching decision to make a switching decision based upon XML transaction information in a received message if the XML checker determines that the message include XML information, the content based message director comprising an output interface to route or direct a received message to one of the processing nodes based upon the switching decision if the message includes XML information, otherwise the content based message director to route or direct the message while bypassing or omitting XML-related processing.

6. A method of XML based switching comprising:

receiving a XML message, the message including business transaction information provided in a XML based language;

determining if the message includes XML information; and performing the following only if the message includes XML information:

XML parsing the message;

comparing the XML business transaction information to one or more configuration patterns;

switching the received XML message to one of a plurality of processing nodes or application servers based upon the comparing.

* * * * *

UNITED STATES PATENT AND TRADEMARK OFFICE
CERTIFICATE OF CORRECTION

PATENT NO. : 6,732,175 B1
DATED : May 4, 2004
INVENTOR(S) : Abjanic

It is certified that error appears in the above-identified patent and that said Letters Patent is hereby corrected as shown below:

Column 12,
Line 32, delete "XNL" and insert -- XML --.

Signed and Sealed this

Thirty-first Day of August, 2004

JON W. DUDAS
*Director of the United States Patent and Trademark Office*